US009714930B2

(12) United States Patent
Jeong et al.

(10) Patent No.: US 9,714,930 B2
(45) Date of Patent: Jul. 25, 2017

(54) APPARATUS AND METHOD FOR MEASURING SALINITY OF INTERSTITIAL WATER COLLECTED FROM SOIL SAMPLE

(71) Applicant: Korea Institute of Geoscience and Mineral Resources, Daejeon (KR)

(72) Inventors: Sueng Won Jeong, Busan (KR); Gil Young Kim, Seoul (KR); Jang-Jun Bahk, Daejeon (KR); Seong-Pil Kim, Daejeon (KR); Sang Hoon Lee, Seoul (KR); Dongyeob Kim, Seoul (KR)

(73) Assignee: KOREA INSTITUTE OF GEOSCIENCE & MINERAL RESOURCES, Daejeon (KR)

(*) Notice: Subject to any disclaimer, the term of this patent is extended or adjusted under 35 U.S.C. 154(b) by 407 days.

(21) Appl. No.: 14/538,373

(22) Filed: Nov. 11, 2014

(65) Prior Publication Data
US 2016/0097730 A1    Apr. 7, 2016

(30) Foreign Application Priority Data
Oct. 2, 2014  (KR) .................. 10-2014-0133360

(51) Int. Cl.
*G01N 33/24* (2006.01)
*G01N 27/07* (2006.01)
*G01N 33/18* (2006.01)

(52) U.S. Cl.
CPC ........... *G01N 33/246* (2013.01); *G01N 27/07* (2013.01); *G01N 33/18* (2013.01); *G01N 33/24* (2013.01)

(58) Field of Classification Search
CPC .......................... G01N 33/24; G01N 33/246
See application file for complete search history.

(56) References Cited

U.S. PATENT DOCUMENTS

2003/0066211 A1*  4/2003  Wang ............... E02D 1/027
                                                        37/347

FOREIGN PATENT DOCUMENTS

KR    10-0441945 B    7/2004
KR    10-0629320 B    9/2006

OTHER PUBLICATIONS

Perera, K.A.R.S., et al., "Vegetation Structure and Species Distribution of Mangroves along a Soil Salinity Gradient in a Micro Tidal Estuary on the North-western Coast of Sri Lanka." American Journal of Marine Science, vol. 1, No. 1 (2013).*

* cited by examiner

Primary Examiner — Paul West
(74) Attorney, Agent, or Firm — Dentons US LLP

(57) ABSTRACT

Disclosed is an apparatus for measuring salinity of interstitial water in a soil sample, the apparatus including: an air supplier that generates a stream of high-pressure air; an air nozzle from which the high-pressure air, supplied from the air supplier, is ejected; a soil-compressing tank into which the high-pressure air, ejected from the air nozzle, is introduced and which compresses a soil sample contained therein to squeeze interstitial water from the soil sample; and a water tank which collects and stores the interstitial water drained from the soil-compressing tank and in which a salinity-measuring sensor for measuring salinity is installed to measure salinity of the interstitial water.

12 Claims, 9 Drawing Sheets

(before changing)　　　(after changing)

APPARATUS AND METHOD FOR MEASURING SALINITY OF INTERSTITIAL WATER COLLECTED FROM SOIL SAMPLE

CROSS REFERENCE TO RELATED APPLICATION DATA

This application is a continuation of Korean Patent Application No. KR 2014-0133360 filed in the Korean Patent Office on Oct. 2, 2014, the entirety of which is incorporated herein by reference to the extent permitted by law.

BACKGROUND OF THE INVENTION

Field of the Invention

The present invention relates to an apparatus and method for measuring salinity of interstitial water collected from a soil sample. More particularly, the present invention relates to an apparatus and method for measuring salinity of interstitial water squeezed from a soil sample by performing the following steps: injecting a stream of high-pressure air into a plurality of soil-compressing tanks that contain the soil sample therein; collecting interstitial water, which is squeezed from the soil sample; measuring salinity of the interstitial water; and obtaining an average value of salinity, thereby enabling determination of engineering characteristics of the soil sample.

At least one of the soil-compressing tanks includes an upper filter assembly and a lower filter assembly, which are stacked sequentially and arranged horizontally or vertically, with a soil sample interposed between the upper filter assembly and the lower filter assembly. When the high-pressure air is supplied through an air nozzle into the soil-compressing tank in which the upper filter assembly, the soil sample, and the lower filter assembly are sequentially stacked, and a middle portion of the soil sample is pushed to create a fault line (also known as shear plane), causing shear stress. This enables not only measurement of the salinity of the interstitial water squeezed from the soil sample but also measurement of the shear strength of the soil sample.

The arrangement, in which at least any one of the soil-compressing tanks is horizontally or vertically arranged and in which the upper filter assembly and the lower filter assembly are sequentially arranged, with the soil sample interposed between the upper filter assembly and the lower filter assembly, also enables measurement of consolidation of the soil sample.

Description of the Related Art

Generally, soils collected from the seabed or a coastal area have different salinity. The salinity affects the engineering characteristics of collected soils.

That is, it is known that salinity affects the structure and arrangement of grains of soils. For example, salinity affects Atterberg limits.

Atterberg limits include the liquid limit and the plastic limit and are important factors in determining the consistency of soil. The liquid limit is defined as the critical water content at which the liquid state (behavior of soil) changes. For example, in the case of illite clay, when its salinity changes from 0 g/L to 30 g/L, its liquid limit also changes. Even with a slight change in salinity, like from 0 g/L to 1 g/L, an increase in the liquid limit is observed.

Meanwhile, highly-swellable clay such as bentonite consisting mostly of montmorillonite tends to exhibit a dramatic decrease in the liquid limit when its salinity increases from 0 g/L to 30 g/L. Therefore, the liquid and plastic limits of soils change according to their salinity.

The consistency of soil is associated with unique shear strength (i.e., engineering characteristic), so the salinity of soil has a great impact on the geotechnical characteristic of soil. Moreover, salinity is also an important factor to be precisely measured for construction of buildings on saline soils, use of saline soils, prevention of disasters attributable to geological features of coastal areas, use of bentonite, and mobilization for submarine landslides.

For this reason, the demand for an apparatus which can extract salt from interstitial water collected from saline soils and measure the salinity of the interstitial water has grown.

To this end, Korean Patent Registration No. 10-0629320 (Patent Document 1), registered on Sep. 21, 2006, discloses an apparatus for measuring salinity using a differential salt sensor. The apparatus includes a differential salt sensor, a power supply means, and a housing. The differential salt sensor has a circuit in which four impedance elements $Z1$, $Z2$, $Z3$, and $Z4$ are connected in a diamond shape and in which opposite corners of the diamond-shaped circuit are connected to a power supply and a detector. When power is supplied to the terminal on the power supply side, the impedance relation "$Z1Z2=Z3Z4$" is establish and the potential difference at the terminal on the detector side becomes zero (0). Therefore, current does not flow, which means the current is in a balanced state. A reference seawater cylinder and a measurement seawater cylinder are connected in the form of a differential bridge to measure the electrical conductivity of reference seawater and measurement seawater. The salinity of the measurement seawater is measured using a difference in electrical conductivity between the reference seawater and the measurement seawater. The reference seawater cylinder includes an upper cover and a lower cover provided with respective electrode plates, with respective insulating plates interposed between the covers and the electrodes. The upper cover can move in the longitudinal direction of the cylinder. Similarly, the measurement seawater cylinder includes an upper cover and a lower cover provided with respective electrode plates, with respective insulating plates interposed between the covers and the electrodes. The measurement seawater cylinder has an opening in the sidewall so that seawater can be introduced into the measurement seawater cylinder. The power supply means supplies AC power to the differential salt sensor. The housing is a casing for encasing the differential salt sensor and the power supply means and has recesses in which the reference seawater cylinder and the measurement seawater cylinder are to be accommodated, respectively.

Korean Patent Registration No. 10-0441945 (Patent Document 2), registered on Jul. 16, 2004, discloses a salinity-measuring device including a digital conversion controller 10, a computer 30, a display/operation unit 20, a conductometric sensor 15, and a humidity sensor 16. The digital conversion controller 10 includes a current transformer 4 that measures current, an A/D converter 5 that converts the value of measured current output from the current transformer 4 into a digital signal, a Digital Signal Processor (DSP) 6 that receives and processes the digital signal output from the A/D converter 5, and a transmitter-receiver 7 that is connected to the DSP 6 to receive and transmit data. The computer 30 receives the signal output from the transmitter-receiver 7, and analyzes and stores the data. The display/operation unit 20 displays data after receiving the data from the DSP 6 through the transmitter-receiver 7, and enables an operation to change a measurement reference value. The conductometric sensor 15 is connected to one input terminal of the current transformer 4 and the humidity sensor 16 is connected to one input terminal of the A/D converter 5.

Despite existence of the related arts, there is still demand for improvement in an apparatus for measuring salinity of interstitial water squeezed from saline soils collected from a coastal area or a seabed and in a method for operating the apparatus.

The foregoing is intended merely to aid in the understanding of the background of the present invention, and is not intended to mean that the present invention falls within the purview of the related art that is already known to those skilled in the art.

DOCUMENTS OF RELATED ART (Patent Document 1) Korean Patent Registration No 10-0629320 (registered on Sep. 21, 2006)
(Patent Document 2) Korean Patent Registration No 10-0441945 (registered on Jul. 16, 2004)

SUMMARY OF THE INVENTION

Accordingly, the present invention has been made keeping in mind the above problems occurring in the related art, and an object of the present invention is to provide an apparatus and method for measuring salinity of interstitial water obtained from a soil sample by injecting a stream of high-pressure air supplied from an external air supplier into a soil-compressing tank in which the soil sample is contained, collecting interstitial water squeezed from the soil sample in a water tank, and measuring salinity of the interstitial water. In this manner, the apparatus can determine engineering characteristics of the soil sample.

Another object of the invention is to provide an apparatus for measuring salinity of interstitial water obtained from a soil sample, the apparatus including at least one soil-compressing tank in which an upper filter assembly and a lower filter assembly are sequentially and horizontally or vertically arranged, with a soil sample interposed therebetween. When a stream of high-pressure air is supplied to the soil-compressing tank through an air nozzle, a middle portion of the soil sample is pushed to create a fault line, causing shear stress, which enables measurement of consolidation of the soil sample as well as measurement of salinity of the interstitial water obtained from the soil sample.

A further object of the invention is to provide an apparatus for measuring salinity of interstitial water obtained from a soil sample, the apparatus including at least one soil-compressing tank in which an upper filter assembly and a lower filter assembly are sequentially and vertically or horizontally stacked, with the soil sample interposed between them, thereby enabling measurement of consolidation of the soil sample.

That is, the objects of the present invention are to provide an apparatus and method for measuring salinity from saline soils, which can measure consolidation of soil as well as salinity of interstitial water contained in saline soil simultaneously.

In order to accomplish the objects of the invention, one aspect provides an apparatus for measuring salinity of interstitial water in a soil sample, the apparatus including: an air supplier which produces a stream of high-pressure air; an air nozzle from which the high-pressure air, supplied from the air supplier, is ejected; a soil-compressing tank into which the high-pressure air ejected from the air nozzle is introduced and which compresses a soil sample contained therein, squeezing interstitial water from the soil sample; and a water tank in which the interstitial water, drained from the soil-compressing tank, is connected and in which a salinity-measuring sensor for measuring salinity of the interstitial water is installed.

In the soil-compressing tank, an upper filter assembly and a lower filter assembly may be sequentially stacked, and a soil sample is placed between the upper filter assembly and the lower filter assembly.

Because of the arrangement in which the upper filter assembly and the lower filter assembly are vertically or horizontally arranged and sequentially stacked, and the soil sample is placed in a gap between the upper filter assembly and the lower filter assembly, when high-pressure air is introduced into the soil-compressing tank through air nozzles, a middle portion of the soil sample is pushed to create a fault line, causing shear stress.

The upper filter assembly has a structure in which a first metal filter, a paper filter, and a second metal filter are sequentially stacked. Similarly, the lower filter assembly has a structure in which a first metal filter, a paper filter, and a second metal filter are sequentially stacked.

The first metal filters each have a plurality of through-holes.

A center portion of the first metal filter of the upper filter assembly, which faces the air nozzle, may be a through-hole-free portion in which through holes are not formed.

That is, in each of the upper filter assembly and the lower filter assembly, a pair of metal filters may be arranged to face each other, with a space therebetween.

The pair of metal filters may be arranged in a manner such that the through-holes of the opposing metal filters are misaligned with each other in a vertical direction.

In order to accomplish the objects of the invention, another aspect provides an apparatus for measuring salinity of interstitial water in a soil sample, the apparatus including: an air supplier that generates a stream of high-pressure air; an air nozzle from which the high-pressure air, supplied from the air supplier, is ejected; a soil-compressing tank into which the high-pressure air, ejected from the air nozzle, is introduced and that compresses a soil sample disposed in a gap between an upper filter assembly and a lower filter assembly, producing interstitial water; and a water tank in which the interstitial water, drained from the soil-compressing tank, is collected, and in which a salinity-measuring sensor for measuring salinity of the interstitial water is installed, wherein a middle portion of the soil sample is pushed to create a fault line by the high-pressure air introduced into the soil-compressing tank connected to the air nozzle, and shear stress generated by the sliding is measured by a load cell disposed on one side of the lower filter assembly.

In order to accomplish the objects of the present invention, a further aspect provides an apparatus for measuring salinity of interstitial water in a soil sample, the apparatus including: an air supplier that generates a stream of high-pressure air; an air nozzle from which the high-pressure air, supplied from the air supplier, is ejected; a soil-compressing tank into which the high-pressure air, ejected from the air nozzle, is introduced, in which a gauge is installed, and that compresses a soil sample disposed in a gap between an upper filter assembly and a lower filter assembly, producing interstitial water; and a water tank in which the interstitial water, drained from the soil-compressing tank, is collected, and in which a salinity-measuring sensor for measuring salinity of the interstitial water is installed, wherein a gap between an upper or lower inside surface of the soil-compressing tank and the sample soil expands with time by the high-pressure air introduced into the soil-compressing tank connected to the air nozzle and the expanded gap is measured by the gauge.

A further aspect provides a method of measuring salinity of interstitial water in a soil sample, the method including: removing an upper filter assembly from a soil-compressing tank; putting a predetermined amount of a soil sample that is collected into the soil-compressing tank from which the upper filter assembly is removed; stacking and pressing the upper filter assembly on and against the upper surface of the soil sample; starting operation of an air supplier; introducing high-pressure air into the soil-compressing tank through an air nozzle in a state in which the upper filter assembly is stacked and pressed; squeezing interstitial water from the soil sample by the introduction of the high-pressure air; collecting the interstitial water in a water tank; measuring salinity of the interstitial water using a salinity-measuring sensor installed on an inside bottom surface of the water tank; and processing data of the measured salinity of the interstitial water stored in the water tank using a computer.

In the air-introducing step in which the high-pressure air is introduced through the air nozzle in a state in which the upper filter assembly is stacked on and pressed against the soil sample, a metal filter of the upper filter assembly may have a through-hole.

In the air-introducing step in which the high-pressure air is introduced through the air nozzle in a state in which the upper filter assembly is stacked on and pressed against the soil sample, a pair of metal filters of the upper filter assembly may be spaced from each other by a spacer and a turbulent stream of the high-pressure air is formed.

The apparatus and method for measuring salinity of interstitial water obtained from a soil sample have an advantage of precisely measuring salinity of the interstitial water by introducing high-pressure air, supplied from an external air supplier, into a soil-compressing tank in which the soil sample is contained, collecting the interstitial water squeezed from the soil sample in a water tank, and measuring salinity of the collected interstitial water.

The apparatus and method for measuring salinity of interstitial water obtained from a soil sample have another advantage of determining engineering characteristics of a soil sample by collecting interstitial water drained from a plurality of soil-compressing tanks in a water tank and measuring salinity of the collected interstitial water.

The apparatus and method for measuring salinity of interstitial water obtained from a soil sample have a further advantage of easily and systematically managing salinity data of soil which is collected from a specific region by measuring salinity using interstitial water collected in a water tank and processing the data of the measured salinity using a computer.

The apparatus and method for measuring salinity of interstitial water obtained from a soil sample have a further advantage of performing simultaneous measurements of salinity of interstitial water contained in a soil sample and consolidation of the soil sample by arranging at least one soil-compressing tank selected from among a plurality of soil-compressing tanks in a horizontal direction or a vertical direction, and by introducing high-pressure air into the horizontally or vertically arranged soil-compressing tank through an air nozzle in a state in which an upper filter assembly is stacked on and pressed against the soil sample in a specific soil-compressing tank, thereby pushing a middle portion of the soil sample to create a fault line by the introduced high-pressure air, resulting in occurrence of shear stress.

In addition, with the arrangement in which at least one soil-compressing tank selected from among a plurality of soil-compressing tanks is horizontally or vertically arranged, in which an upper filter assembly and a lower filter assembly are installed in the horizontally or vertically arranged soil-compressing tank, and in which a soil sample is disposed between the upper filter assembly and the lower filter assembly, it is possible to measure consolidation of the soil sample by measuring the degree of compression of the soil sample attributable to an air pressure applied to the soil-compressing tank.

BRIEF DESCRIPTION OF THE DRAWINGS

The above and other objects, features and other advantages of the present invention will be more clearly understood from the following detailed description when taken in conjunction with the accompanying drawings, in which.

DESCRIPTION OF THE PRESENTLY PREFERRED EMBODIMENTS

Figure 1:
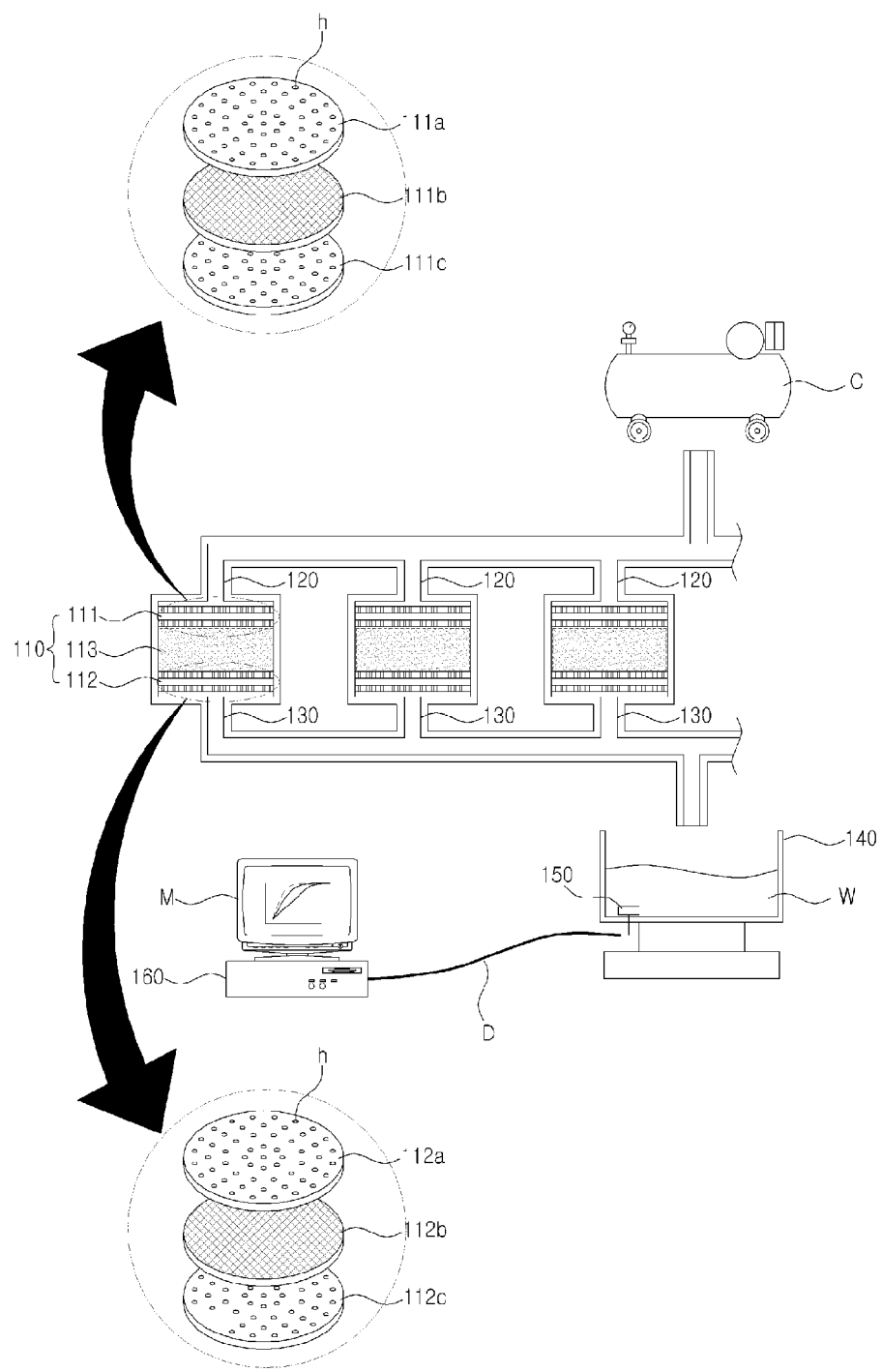
FIG. 1 is a schematic diagram illustrating an apparatus for measuring the salinity of interstitial water in a soil sample (simply referred to as salinity-measuring apparatus) according to an embodiment of the invention.

Hereinafter, preferred embodiments of the present invention are described with reference to the accompanying drawings. Any specific description about functions or constructions that is well known in related arts will be omitted, when such a description is likely to obscure the gist of the present invention.

Reference will now be made in detail to various embodiments of the present invention, specific examples of which are illustrated in the accompanying drawings and described below, since the embodiments of the present invention can be variously modified in many different forms.

While the present invention will be described in conjunction with exemplary embodiments thereof, it is to be understood that the present description is not intended to limit the present invention to those exemplary embodiments. On the contrary, the present invention is intended to cover not only the exemplary embodiments, but also various alternatives, modifications, equivalents and other embodiments that may be included within the spirit and scope of the present invention as defined by the appended claims.

It will be understood that when an element is referred to as being "coupled" or "connected" to another element, it can be directly coupled or connected to the other element or intervening elements may be present therebetween. In contrast, it should be understood that when an element is referred to as being "directly coupled" or "directly connected" to another element, there are no intervening elements present. Other expressions that explain the relationship between elements, such as "between," "directly between," "adjacent to," or "directly adjacent to," should be construed in the same way.

The terminology used herein is for the purpose of describing particular embodiments only and is not intended to be limiting. As used herein, the singular forms "a," "an" and "the" are intended to include the plural forms as well, unless the context clearly indicates otherwise. It will be further understood that the terms "comprise", "include", "have", etc. when used in this specification, specify the presence of stated features, integers, steps, operations, elements, components, and/or combinations of them but do not preclude the presence or addition of one or more other features, integers, steps, operations, elements, components, and/or combinations thereof.

Throughout the drawings, the same reference numerals will refer to the same or like parts.

FIG. 1 is a schematic diagram illustrating an "apparatus for measuring the salinity of interstitial water in a soil sample", which will be occasionally, simply referred to as "salinity-measuring apparatus", according to a first embodiment.

As illustrated in FIG. 1, the salinity-measuring apparatus according to the first embodiment includes: an air supplier C (i.e., a compressor) that generates a stream of high-pressure air; a soil-compressing tank 110 into which the high-pressure air is introduced from the air supplier C and in which an upper filter assembly 111, a soil sample 113, and a lower filter assembly 112 are arranged in this order. The salinity-measuring apparatus according to the first embodiment determines engineering characteristics of the soil sample using interstitial water W squeezed from the sample soil by the high-pressure air.

Hereinbelow, the construction of each element, the operational association between the elements, and effects of the salinity-measuring apparatus according to the first embodiment will be described with reference to FIG. 1.

As illustrated in FIG. 1, a stream of high-pressure air is generated by the air supplier C, and the generated high-pressure air stream is guided through a plurality of air nozzles 120 and ejected from the air nozzles 120 as a plurality of streams of high-pressure air. The streams of high-pressure air push the soil sample 113 contained in the soil-compressing tank 110, compressing the soil sample and producing interstitial water W.

The interstitial water W drained from the soil-compressing tank 110 is collected in a water tank 140, and a salinity-measuring sensor 150 installed in the water tank 140 measures the salinity of the interstitial water W.

In the soil-compressing tank 110, the upper filter assembly 111, the soil sample 113, and the lower filter assembly are stacked in this order.

The upper filter assembly 111 includes a first metal filter 111a, a paper filter 111b, and a second metal filter 111c which are sequentially stacked. Similarly, the lower filter assembly 112 includes a first metal filter 112a, a paper filter 112b, and a second metal filter 112c which are sequentially stacked.

Each of the first metal filters 111a and 112a has a plurality of through-holes h. A center portion of the first metal filter 111a for the upper filter assembly, which faces the air nozzle 120, may be provided with no through-holes. So, the center portion of the first upper metal filter 111a is referred to as through-hole-free region R.

This arrangement, in which the first metal filters 111a and 112a and the second metal filters 111c and 112c are disposed at outer sides of the upper filter assembly 111 and the filter assembly 112 and in which the paper filters 111b and 112b are interposed between the first metal filters 111a and 112a and the second metal filters 111c and 112c, prevents the soil sample from flying out of or escaping the soil-compressing tank 110 when the interstitial water in pores of the soil sample 113 is squeezed by the stream of high-pressure air. Specifically, the paper filters 111b and 112b can prevent the soil sample from flying or escaping. The paper filters 111b and 112b are likely to rupture, when only the paper filters 111b and 112b are disposed on the outer surfaces of the soil sample 113. In order to prevent this, the first metal filters 111a and 112a and the second metal filters 111c and 112c are disposed on the outer surfaces of the respective paper filters 111b and 112b.

The first metal filter 111a has a center portion facing the air nozzle 120. The center portion is not provided with the through-holes h so that the center portion of the first metal filter 111a is referred to as through-hole-free portion R. The through-hole-free portion R prevents the high-pressure air from passing through the center portion at which the shortest air path is likely to be formed in a case where the through-holes h are uniformly distributed over the entire area of the first metal filter 111a, when the high-pressure air is ejected from the air nozzle 120. In this case, it is difficult to intensively extract interstitial water from pores in the soil sample 113. For this reason, the high-pressure air is guided to move along the wall of the soil-compressing tank 110 by preventing the high-pressure air from moving through the center portion of the metal filter, thereby uniformly extracting the interstitial water in the soil sample 113 over the entire area of the soil sample.

In each of the upper filter assembly 111 and the lower filter assembly 112, a pair of metal filters, arranged to face each other, are spaced from each other by a spacer S. The metal filters are arranged in a manner such that the corresponding through-holes h formed in the spaced metal filters are misaligned with each other in a vertical direction.

That is, the high-pressure air ejected from the air nozzle 120 is guided to the soil sample 113 through the upper filter assembly 111. At this point, since the through-holes h are arranged in a zigzag form, a turbulent air stream is formed while the high-pressure air is passing through the pair of metal filters in the filter assembly. This arrangement is an effective way to more effectively squeeze the interstitial water W because it makes the high-pressure air pass through more pores of the soil sample.

Figure 7:
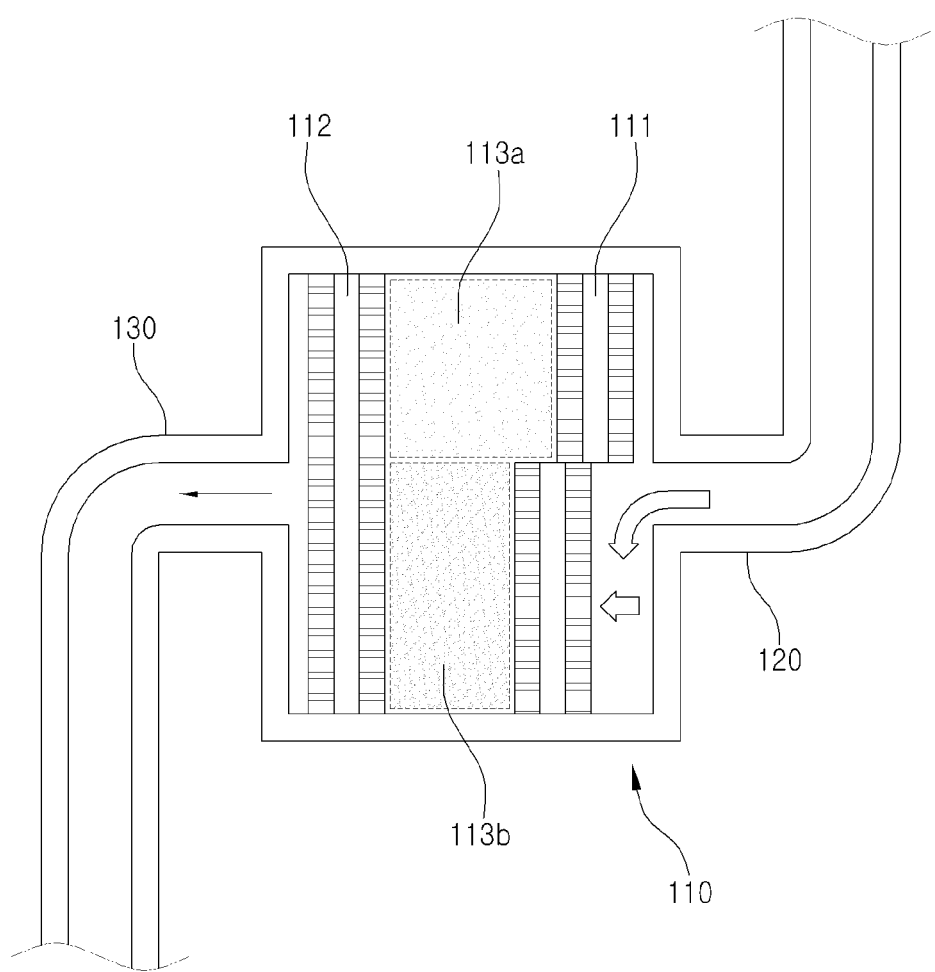
FIG. 7 is a schematic diagram illustrating a shear phenomenon generated in a horizontally-arranged soil-compressing tank of a plurality of soil-compressing tanks, in an apparatus for measuring the salinity of interstitial water contained in a soil sample according to an embodiment of the invention.
Figure 8:
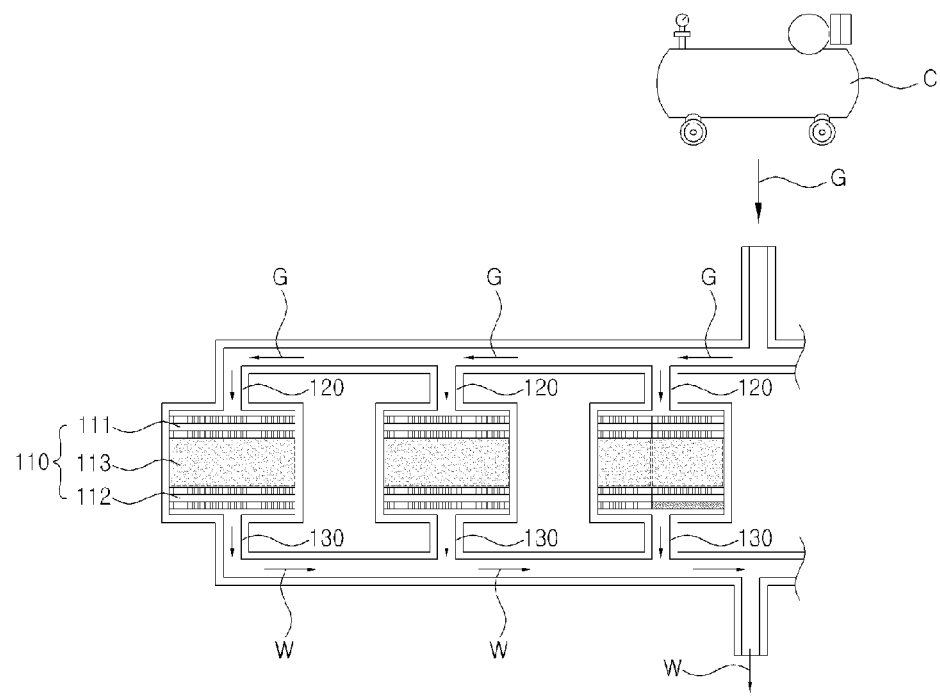
FIG. 8 is a schematic diagram illustrating a shear phenomenon generated in a vertically-arranged soil-compressing tank of a plurality of soil-compressing tanks according to an embodiment of the invention.
Figure 8:
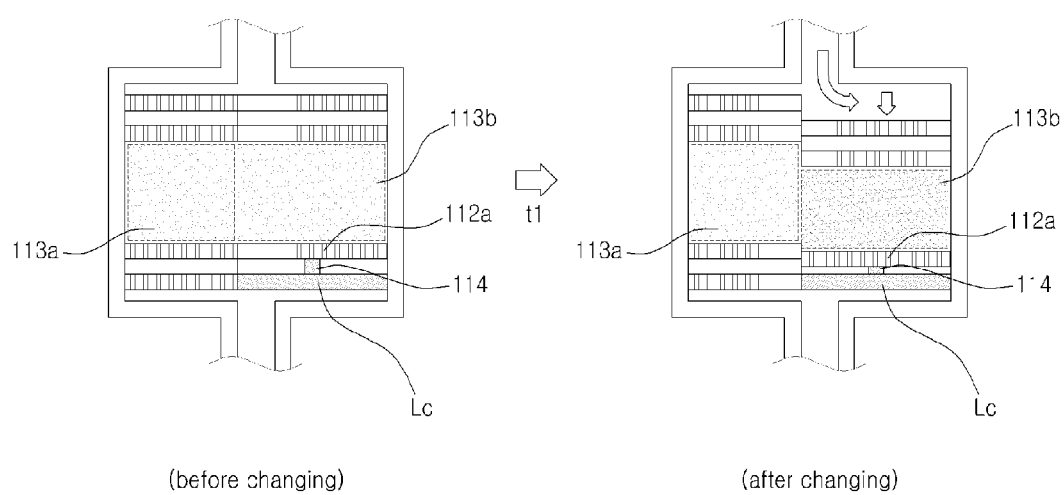

Besides the structure illustrated in FIG. 1, the apparatus for measuring salinity of interstitial water contained in a soil sample may be structured as illustrated in FIG. 7 or 8. That is, at least one soil-compressing tank selected from among a plurality of soil-compressing tanks is horizontally or vertically arranged. Furthermore, the upper filter assembly and the lower filter assembly are sequentially stacked, and the soil sample is disposed in a gap between the upper filter assembly and the lower filter assembly. Therefore, when the high-pressure is supplied through the air nozzle, a middle portion of the soil sample is pushed to create a fault line by the pressure of the high-pressure air, causing shear stress or consolidation of the soil sample as illustrated in FIG. 9.

Figure 9:
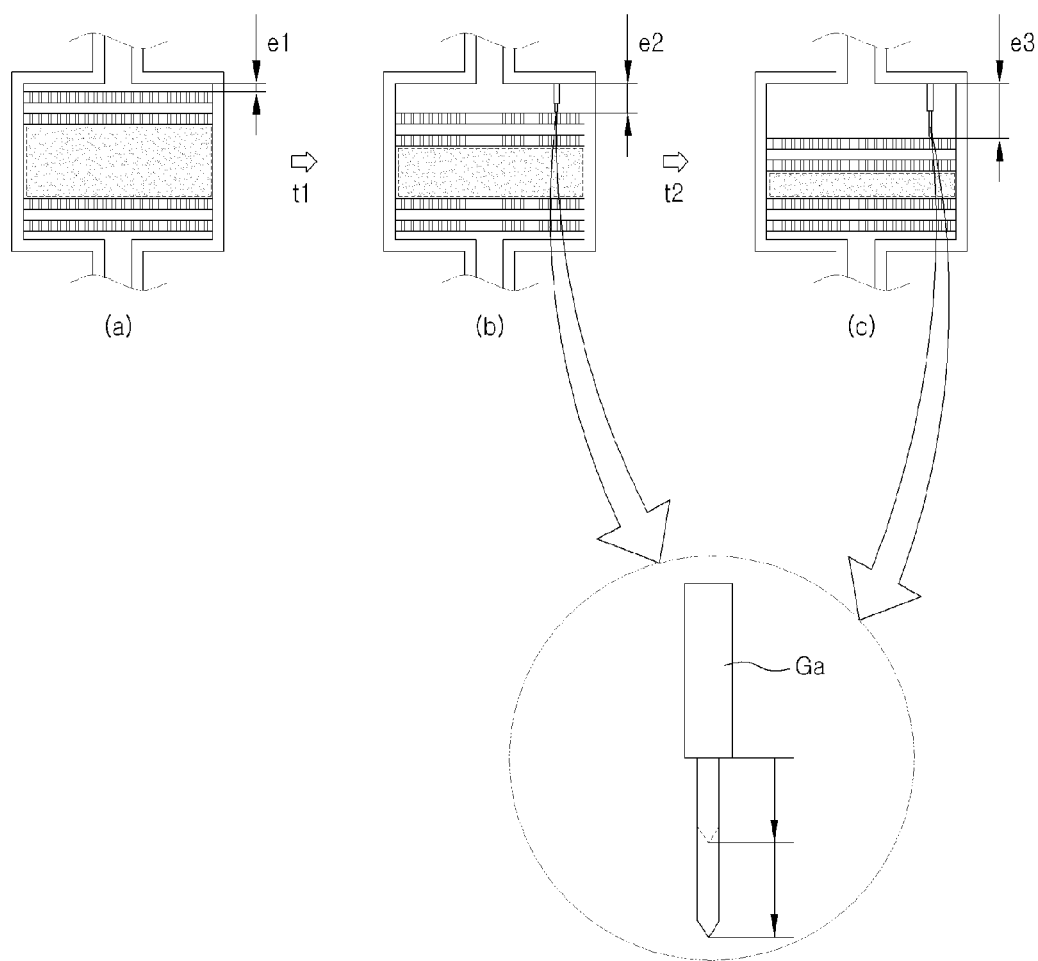
FIG. 9 is a schematic diagram illustrating a consolidation phenomenon generated in a soil-compressing tank of a plurality of soil-compressing tanks according to an embodiment of the invention.

As described above, at least one soil-compressing tank is structured to measure shear stress as illustrated in FIGS. 7 and 8, or structured to measure consolidation of the soil sample as illustrated in FIG. 9. This structure can form a system that can simultaneously perform measurement of shear stress and/or consolidation of the soil sample, and measurement of salinity of interstitial water of the soil sample.

Figure 2:
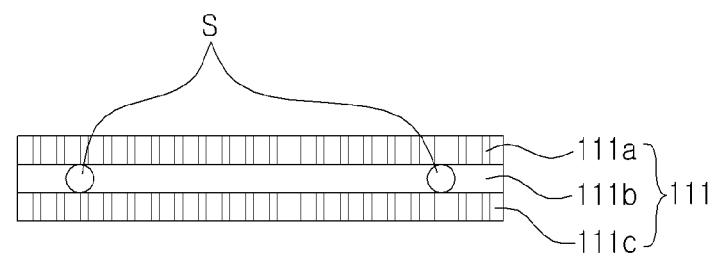
FIG. 2 is a schematic diagram illustrating a process of putting a soil sample into a soil-compressing tank of the salinity measuring apparatus according to an embodiment of the invention.
Figure 2:
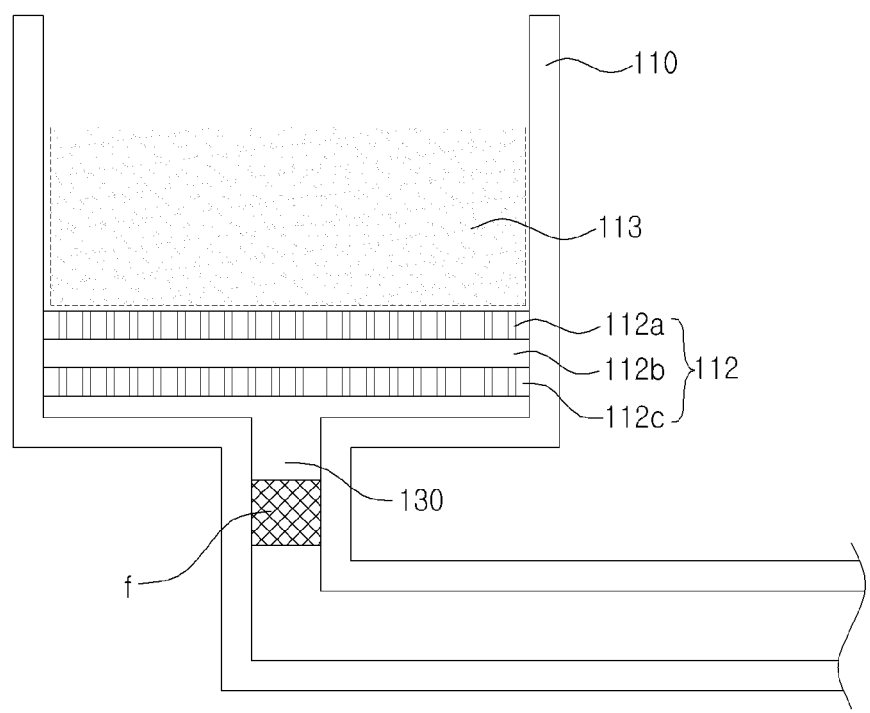

FIG. 2 is a schematic diagram illustrating a process of putting a soil sample into the soil-compressing tank in the salinity-measuring apparatus according to the present invention.

As illustrated in FIG. 2, the salinity-measuring apparatus according to the first embodiment is prepared to measure salinity of interstitial water in the soil sample by opening an upper cover of the soil-compressing tank 110, putting a sufficient amount of the soil sample 113 into the soil-compressing tank 110 from an upper side of the lower filter assembly 112, and stacking the removed upper filter assembly 111 on the soil sample 113.

Figure 3:
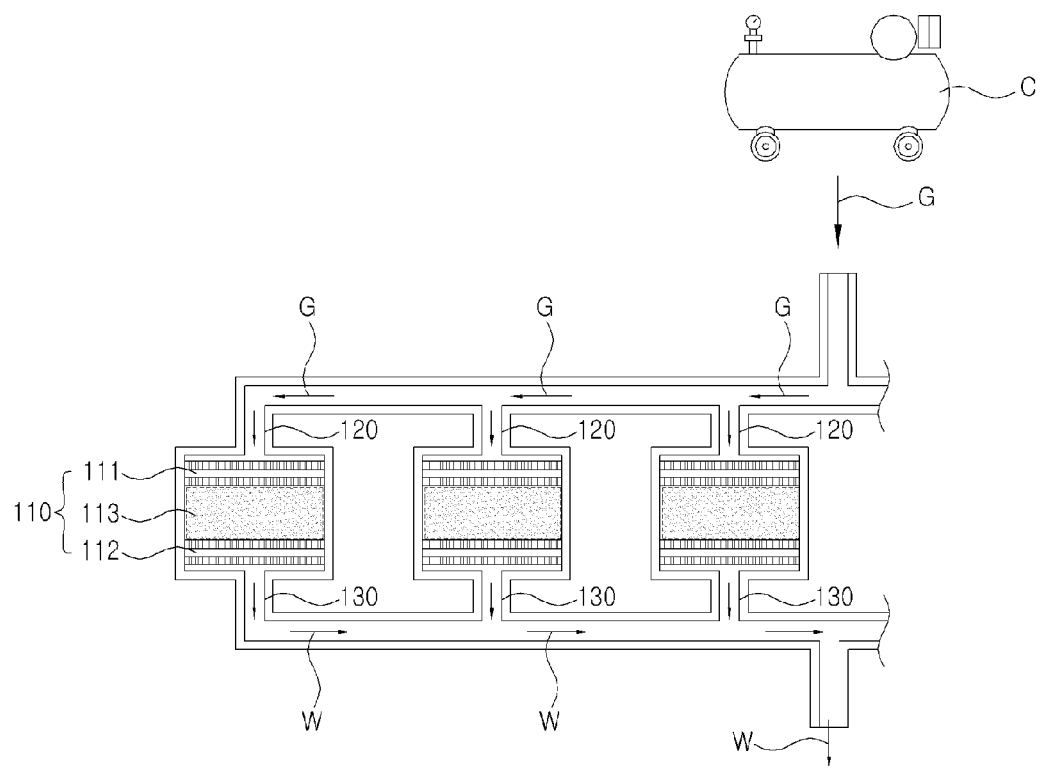
FIG. 3 is a schematic diagram illustrating a process of squeezing interstitial water from the soil sample contained in the soil-compressing tank by introducing high-pressure air into the soil-compressing tank through an air nozzle according to an embodiment of the invention.

FIG. 3 is a schematic diagram illustrating a process of squeezing interstitial water from the soil sample using the high-pressure air supplied through the air nozzle in a state in which the soil sample is contained in the soil-compressing tank.

As illustrated in FIG. 3, pores are formed in a sufficient amount of the soil sample and interstitial water W is stored in the pores. According to the salinity-measuring apparatus according to one embodiment, since the interstitial water W is stored in the pores, when high-pressure air is supplied to the sufficient amount of soil sample 113 from the air supplier C, the interstitial water W is guided along an interstitial water discharging nozzle 130 from the pores and is discharged downward.

Figure 4:
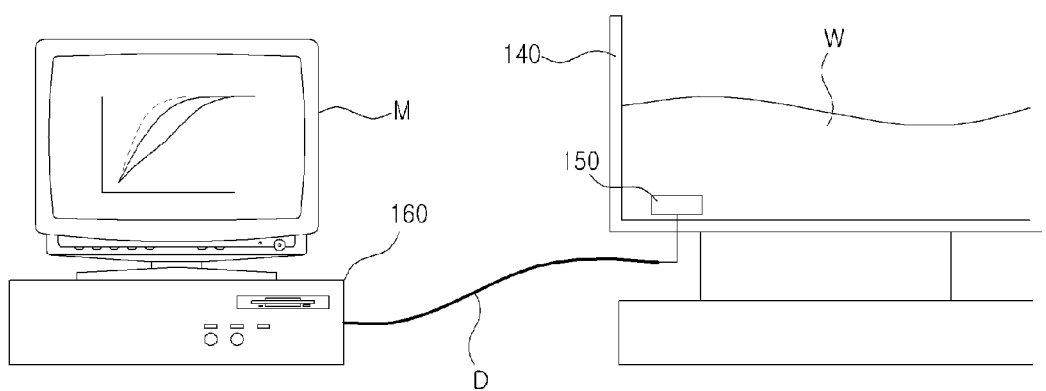
FIG. 4 is a schematic diagram illustrating a process of measuring the salinity of interstitial water collected in a water tank according to an embodiment of the invention.

FIG. 4 is a schematic diagram illustrating a process of measuring salinity of interstitial water connected in a water tank.

As illustrated in FIG. 4, the salinity-measuring apparatus includes the soil-compressing tank 110 from which the interstitial water W is produced, and the water tank 140 which stores the interstitial water W drained from the soil-compressing tank 110 and in which the salinity-measuring sensor 150 for measuring salinity of the interstitial water W is installed.

Therefore, according to one embodiment, the salinity of the interstitial water W stored in the water tank 140 is measured by the salinity-measuring sensor 150, the measured salinity of the interstitial water W is processed by the computer 160, and the processed salinity of the interstitial water W is displayed in the form of a graph on a computer monitor M. Therefore, measurement data of the salinity of a soil sample collected from a specific region can be easily, systematically managed.

Figure 5:
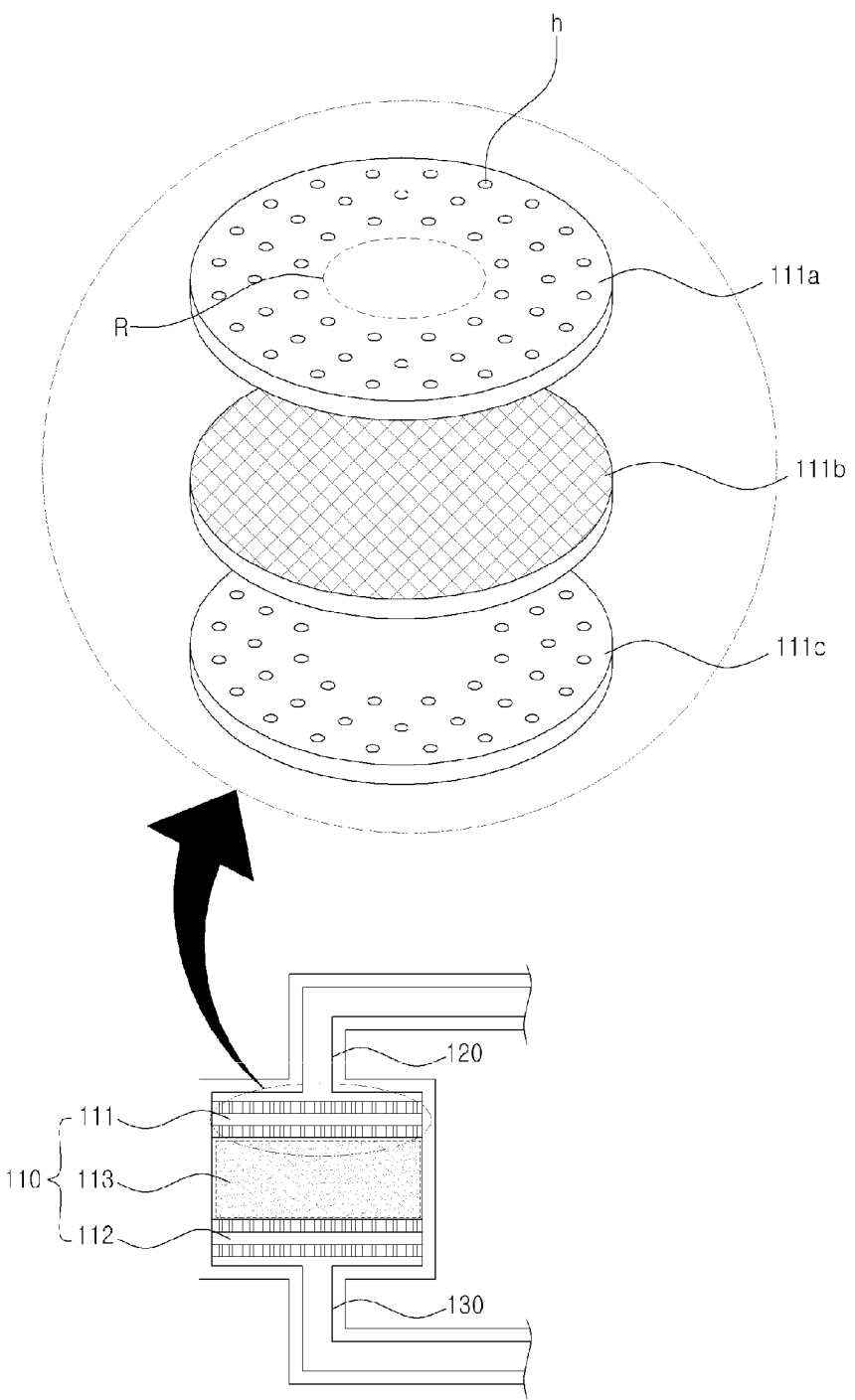
FIG. 5 is a schematic diagram illustrating an apparatus for measuring the salinity of interstitial water in a soil sample according to an embodiment of the invention and illustrating an upper filter assembly with a cover.

FIG. 5 is a schematic diagram illustrating an apparatus for measuring salinity of interstitial water in a soil sample according to a second embodiment, and an upper filter assembly with a cover.

As illustrated in FIG. 5, a first metal filter 111a has a through-hole-free portion R that faces an air nozzle 120 at the center thereof, unlike the structure in which first metal filters 111a and 112a have a plurality of through-holes h.

As described above, the through-hole-free portion R functions as a blocking means. The blocking means makes a large amount of high-pressure air flow downward through a plurality of through-holes h formed around the through-hole-free portion R, so the interstitial water W is effectively extracted from the pores of a soil sample.

Figure 6:
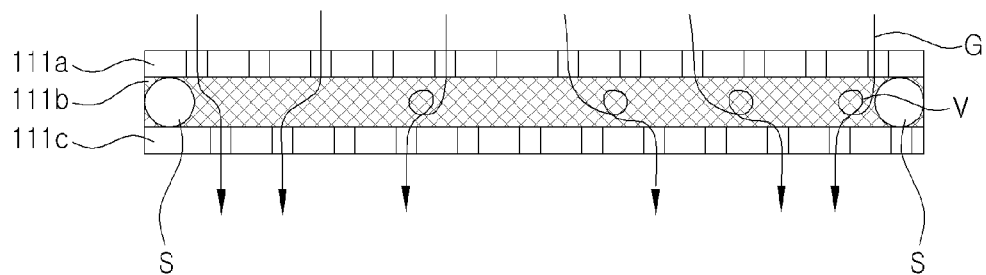
FIG. 6 is a schematic diagram illustrating an apparatus for measuring the salinity of interstitial water in a soil sample according to an embodiment of the invention and illustrating an upper filter assembly and a process of creating turbulence of the interstitial water.

FIG. 6 is a schematic diagram illustrating an apparatus for measuring salinity of interstitial water in a soil sample according to a third embodiment and illustrating creation of a turbulent stream of air using an upper filter assembly with a spacer.

As illustrated in FIG. 6, the upper filter assembly 111 and the lower filter assembly 112 each have a structure in which a pair of metal filters T are spaced from each other by a spacer S, and through-holes h of the metal filters T, which correspond to each other, are misaligned in a vertical direction.

That is, the through-holes h of the metal filters T, which correspond to each other, respectively, are misaligned with each other in a vertical direction but arranged in a zigzag form, and a turbulent stream of air V is formed while air is passing through each of the upper filter assembly 111 and the lower filter assembly 112, each provided with a spacer S therein. Therefore, the interstitial water W is more effectively extracted from the pores.

The apparatus for measuring the salinity of interstitial water obtained from a soil sample is used to measure salinity. The salinity of the interstitial water is measured using the salinity-measuring apparatus in the following order: a step (S110) of removing an upper filter assembly 111; a step (S120) of putting a predetermined amount of a soil sample 113 into each soil-compressing tank 110 from which the upper filter assembly 111 is removed; a step (S130) of stacking and pressing the upper filter assembly 111 on and against an upper surface of the soil sample contained in the soil-compressing tank; a step (S140) of starting operation of an air supplier C; a step (S150) of supplying high-pressure air to each soil-compressing tank through an air nozzle 120 in a state in which the upper filter assembly 111 is stacked and pressed; a step (S160) at which interstitial water W is squeezed from the soil sample 113 and discharged downward by the high-pressure air; a step (S170) at which the discharged interstitial water W is collected in a water tank 140; a step (S180) at which a salinity-measuring sensor 150 installed in the water tank 140 measures salinity after collection of the interstitial water W is completed; and a step (S190) of processing data of the measured salinity for the interstitial water W collected in the water tank 140.

As to the step at which the high-pressure air is supplied through each air nozzle 120 in the state in which the upper filter assembly 111 is stacked and pressed, metal filters 111a, 111c, and T forming the upper filter assembly 111 have through-holes h.

As to the step at which the high-pressure air is supplied through each air nozzle 120 in the state in which the upper filter assembly 111 is stacked and pressed, a pair of metal filters T, which are elements of the upper filter assembly 111, are spaced from each other by a spacer S, so a turbulent stream of air is formed.

FIG. 7 is a schematic diagram illustrating a shear phenomenon generated in a horizontally arranged soil-compressing tank of a plurality of soil-compressing tanks in an apparatus for measuring salinity of interstitial water in a soil sample, and FIG. 8 is a schematic diagram illustrating a shear phenomenon generated in a vertically arranged soil-compressing tank of the plurality of soil-compressing tanks.

That is, according to the apparatus for measuring salinity of interstitial water in a soil sample according to a further embodiment of the present invention illustrated in FIGS. 7 and 8, when high-pressure air is supplied through an air nozzle 120 in a state in which an upper filter assembly 111 is stacked or pressed in the horizontally arranged soil-compressing tank of the plurality of soil-compressing tanks, a middle portion of a soil sample 113 is pushed to create a fault line, causing shear stress.

According to the apparatus for measuring salinity of interstitial water in a soil sample according to the embodiment of the present invention, it is possible to not only measure the salinity of interstitial water contained in a soil sample but also measure the shear stress of the soil sample at the same time using the horizontally or vertically arranged soil-compressing tank of the plurality of soil-compressing tanks.

In the case of measuring the shear stress of the soil sample using the horizontally or vertically arranged soil-compressing tank of the plurality of soil-compressing tanks, it can be observed that shear stress occurs in a surface of the soil sample directly under the air nozzle 120 (see FIG. 8) or near the air nozzle (see FIG. 7).

As illustrated in FIG. 8, a load cell Lc is installed on one side of the lower filter assembly 112 in which a shear phenomenon occurs. As illustrated in a figure (captioned "before changing") on the left side of FIG. 8, since high-pressure air is supplied at an early stage before the shear phenomenon occurs, a middle portion of the soil sample 113 is pushed to create a fault line, and the shear stress generated in this course is measured by the load cell Lc.

To be specific, a soil sample 113a (113b) is horizontally arranged before the shear stress occurs. However, when the soil-sample 113b is pressed through the pressure of air supplied through the air nozzle 120 disposed right above the soil sample 113b, a middle portion of the soil sample 113 is pushed to create a fault line, causing shear stress. This state is illustrated in a figure (captioned "after changing") on the right side of FIG. 8.

The shear stress is measured when the soil sample 113b, which is pushed to create a fault line, and when the force generated by the sliding is applied to the load cell Lc connected by the first metal filter 112a and a connection member 114.

In the apparatus for measuring salinity of interstitial water in a soil sample according to the present invention, the high-pressure air ejected from the air nozzle 120 is transferred to the soil sample 113 through the upper filter assembly 111.

The upper filter assembly 111 has a predetermined thickness and has no through-holes. Preferably, the upper filter assembly may be made of a material which will not be deformed by the pressure of air.

FIG. 9 is a schematic diagram illustrating a consolidation phenomenon in the vertically arranged soil-compressing tank of the plurality of soil-compressing tanks.

As illustrated in FIG. 9, according to the apparatus for measuring salinity of interstitial water in a soil sample according to a further embodiment, when the high-pressure air is supplied through the air nozzle 120 in the state in which the upper filter assembly 111 is stacked and pressed in the vertically arranged soil-compressing tank of the plurality of soil-compressing tanks, an initial distance e1 between the wall of the soil-compressing tank and the soil sample 113 changes to increase and the distance becomes e2 after a period of time t1 elapses. Finally, the distance increases with time and finally becomes e3 after a time t2 elapses. The distances e2 and e3 can be measured using an additional gauge Ga. With the measurement of the distance between the soil sample and the wall of the soil-compressing tank, consolidation of the soil sample can be measured.

According to the apparatus and method for measuring salinity of interstitial water in a soil sample described above, the high-pressure air, supplied from an external air supplier C, is introduced into the soil-compressing tank 110 in which the soil sample 113 is contained, and the interstitial water W squeezed from the soil sample 113 is collected in the water tank 140. So, the salinity can be precisely measured using the collected interstitial water W.

According to the apparatus and method for measuring salinity of interstitial water in a soil sample described above, the interstitial water W drained from the plurality of soil-compressing tanks 110 and collected in the water tank 140 is used to measure salinity. Accordingly, it is possible to determine engineering characteristics of the soil sample 113.

According to the apparatus and method for measuring salinity of interstitial water in a soil sample described above, the interstitial water W drained from the plurality of soil-compressing tanks 110 and collected in the water tank 140 is used to measure salinity, and data of measured salinity is processed using a computer 160. In this way, it is possible to easily and systematically manage the measured salinity and data related to measured salinity for the soil sample 113 collected from a specific region.

According to the apparatus and method for measuring salinity of interstitial water in a soil sample described above, in a specific soil-compressing tank 110 that is horizontally arranged, the high-pressure air is supplied through the air nozzle in the state in which the upper filter assembly 111 is stacked and pressed. Therefore, a middle portion of the soil sample 113 is pushed to create a fault line by the pressure of the high-pressure air, causing shear stress. Accordingly, it is possible to measure the salinity of interstitial water in a soil sample and the shear strength of the soil sample simultaneously.

Those who are ordinarily skilled in the art will appreciate that various alternatives, modifications, and equivalents are possible, without changing the spirit or essential features of the present invention.

Therefore, preferred embodiments of the present invention have been described for illustrative purposes, and should not be construed as being restrictive.

The scope of the present invention is defined by the accompanying claims rather than the description which is presented above. Moreover, the present invention is intended to cover not only the exemplary embodiments, but also various alternatives, modifications, equivalents and other embodiments that may be included within the spirit and scope of the present invention as defined by the appended claims.

What is claimed is:

1. An apparatus for measuring salinity of interstitial water in a soil sample, comprising:

an air supplier that generates a stream of high-pressure air;
an air nozzle from which the high-pressure air, supplied from the air supplier, is ejected;
a soil-compressing tank into which the high-pressure air, ejected from the air nozzle, is introduced and that compresses a soil sample contained therein to squeeze interstitial water from the soil sample; and
a water tank that collects and stores the interstitial water drained from the soil-compressing tank and in which a salinity-measuring sensor for measuring salinity is installed to measure salinity of the interstitial water, wherein,
in the soil-compressing tank, an upper filter assembly and a lower filter assembly are sequentially stacked and the soil sample is disposed in a gap between the upper filter assembly and the lower filter assembly.

2. The apparatus according to claim 1, wherein the upper filter assembly and the lower filter assembly are sequentially stacked and horizontally or vertically arranged, the soil sample is stacked in the gap between the upper filter assembly and the lower filter assembly, and a middle portion of the soil sample is pushed to create a fault line by a pressure of the high-pressure air supplied through the air nozzle, causing shear stress.

3. The apparatus according to claim 1, wherein the upper filter assembly and the lower filter assembly have a structure in which a first metal filter, a paper filter, and a second metal filer are sequentially stacked.

4. The apparatus according to claim 3, wherein the first metal filters of the upper filter assembly and the lower filter assembly have a plurality of through-holes.

5. The apparatus according to claim 4, wherein the first metal filter of the upper filter assembly has a through-hole-free portion facing the air nozzle in a center portion thereof.

6. The apparatus according to claim 1, wherein the upper filter assembly and the lower filter assembly have a structure in which two metal filters are spaced by a spacer.

7. The apparatus according to claim 6, wherein the metal filters of the pair of metal filters have holes that can be aligned, but the pair of metal filters are arranged so that the through-holes of the metal filters are not aligned with each other.

8. An apparatus for measuring salinity of interstitial water in a soil sample, comprising:
an air supplier that generates a stream of high-pressure air;
an air nozzle from which the high-pressure air, supplied from the air supplier, is ejected;
a soil-compressing tank into which the high-pressure air, ejected from the air nozzle, is introduced and that compresses a soil sample disposed in a gap formed between an upper filter assembly and a lower filter assembly, producing interstitial water; and
a water tank in which the interstitial water, drained from the soil-compressing tank, is collected and in which a salinity-measuring sensor for measuring salinity of the interstitial water is installed,
wherein,
a middle portion of the soil sample is pushed by the high-pressure air introduced into the soil-compressing tank connected to the air nozzle, creating a fault line in the soil sample, and shear stress applied to the soil sample is measured by a load cell installed on one side of the lower filter assembly.

9. An apparatus for measuring salinity of interstitial water in a soil sample, comprising:
an air supplier that generates a stream of high-pressure air;
an air nozzle from which the high-pressure air, supplied from the air supplier, is ejected;
a soil-compressing tank into which the high-pressure air, ejected from the air nozzle, is introduced and that compresses a soil sample disposed in a gap formed between an upper filter assembly equipped with a gauge and a lower filter assembly, producing interstitial water; and
a water tank in which the interstitial water, drained from the soil-compressing tank, is collected and in which a salinity-measuring sensor for measuring salinity of the interstitial water is installed,
wherein,
a distance between a wall of the soil-compressing tank and the soil sample increases with time due to the high-pressure air introduced into the soil-compressing tank connected to the air nozzle and the distance is measured by the gauge to determine consolidation of the soil sample.

10. A method for measuring salinity of interstitial water in a soil sample, comprising:
removing an upper filter assembly from a soil-compressing tank;
putting a predetermined amount of collected soil sample into the soil-compressing tank from which the upper filter assembly is removed;
stacking and pressing the upper filter assembly on and against an upper surface of the soil sample;
starting operation of an air supplier;
introducing high-pressure air to the soil-compressing tank through an air nozzle in a state in which the upper filter assembly is stacked on and pressed against the soil sample;
squeezing interstitial water contained in the soil sample using a pressure of the high-pressure air and draining the interstitial water;
collecting the drained interstitial water in a water tank;
measuring salinity of the interstitial water stored in the water tank using a salinity-measuring sensor after collection of the interstitial water is completed; and
processing data of the measured salinity of the collected interstitial water stored in the water tank.

11. The method according to claim 10, wherein in the step of introducing the high-pressure air through the air nozzle in a state in which the upper filter assembly is stacked and pressed, a metal filter of the upper filter assembly has a through-hole.

12. The method according to claim 10, wherein in the step of introducing the high-pressure air through the air nozzle in the state in which the upper filter assembly is stacked and pressed, two metal filters of the upper filter assembly are spaced by a spacer, and a turbulent stream of air is formed thereby.

* * * * *